(12) United States Patent
Seifarth et al.

(10) Patent No.: US 8,932,571 B2
(45) Date of Patent: Jan. 13, 2015

(54) SKIN CARE PRODUCT

(75) Inventors: Federico G. Seifarth, Westlake, OH (US); Julia Lax, Brüggen (DE)

(73) Assignee: Alfa Biogene International B.V. (DE)

( * ) Notice: Subject to any disclaimer, the term of this patent is extended or adjusted under 35 U.S.C. 154(b) by 135 days.

(21) Appl. No.: 13/255,572

(22) PCT Filed: Mar. 9, 2010

(86) PCT No.: PCT/EP2010/052948
§ 371 (c)(1),
(2), (4) Date: Mar. 21, 2012

(87) PCT Pub. No.: WO2010/102988
PCT Pub. Date: Sep. 16, 2010

(65) Prior Publication Data
US 2011/0318400 A1 Dec. 29, 2011

(30) Foreign Application Priority Data

Mar. 10, 2009 (EP) ..................... 09154799

(51) Int. Cl.
*A61K 31/64* (2006.01)
*A61Q 19/08* (2006.01)
*A61K 8/64* (2006.01)

(52) U.S. Cl.
CPC . *A61Q 19/08* (2013.01); *A61K 8/64* (2013.01); *A61K 8/645* (2013.01)
USPC ...................................... 424/78.03

(58) Field of Classification Search
CPC .................................. A61K 38/011
USPC ....................................... 530/370
See application file for complete search history.

(56) References Cited

U.S. PATENT DOCUMENTS

| | | | | |
|---|---|---|---|---|
| 5,348,945 A | * | 9/1994 | Berberian et al. | 514/1.9 |
| 5,770,223 A | * | 6/1998 | Bonte et al. | 424/450 |
| 2006/0104934 A1 | * | 5/2006 | Lubrano et al. | 424/70.14 |
| 2008/0249064 A1 | * | 10/2008 | Paufique | 514/54 |

FOREIGN PATENT DOCUMENTS

| | | | |
|---|---|---|---|
| DE | WO 02/055049 | * | 7/2002 |
| EP | 1531160 A1 | | 11/2003 |
| WO | 00/70932 A1 | | 11/2000 |
| WO | 02/055049 A1 | | 7/2002 |
| WO | 02/098910 A1 | | 12/2002 |
| WO | WO 02098910 A1 | * | 12/2002 |

OTHER PUBLICATIONS

Machine translation of WO 02/055049.*
He et al. Acta Biochimica et Biophysica Sinica, Mar. 2008, vol. 40, No. 3, pp. 209-216, Abtract.*
Machine Translation of WO 02/055049, accessed online Nov. 29, 2012.*
PCT/EP2010/052948 International Search Report, (2010).
English Abstract FR 2809308, (2001).
English Abstract FR 2810241, (2001).
English Abstract FR 2792832, (2000).
English Abstract FR 2835746, (2003).
English Abstract FR 2924613, (2009).
English Abstract JP 2004331602, (2004).
Chemical Abstract of: Dal Farra, et al., "Heat Shock Proteins for Cosmeceuticals," (2005).

* cited by examiner

*Primary Examiner* — Benjamin Packard
(74) *Attorney, Agent, or Firm* — Banner & Witcoff, Ltd.

(57) ABSTRACT

The invention relates to a skin-care product comprising at least one component selected from the group of heat shock protein from alfalfa and heat shock protein hydrolysate from alfalfa. The invention further relates to the use of shock protein from alfalfa or hydrolysate thereof for slowing down the aging of the skin and/or for rejuvenating the skin.

34 Claims, No Drawings

SKIN CARE PRODUCT

RELATED APPLICATION DATA

This application is a National Stage Application under 35 U.S.C. 371 of co-pending PCT application PCT/EP2010/052948 designating the United States and filed Mar. 9, 2010; which claims the benefit of EP patent application number 09154799.2 and filed Mar. 10, 2009 each of which are hereby incorporated by reference in their entireties.

The invention relates to a skin care product comprising a heat shock protein.

Heat shock proteins (HSPs) are formed by micro-organisms, plants and animals especially when, as a result of a change in the environment such as exposure to heat, radiation or chemicals, so-called stress-susceptible genes are expressed. According to current insights, such proteins can contribute to protection of cells or tissue of the respective organism, in particular when such environmental changes are harmful or detrimental to the cells or tissue. For that reason, heat shock proteins and the use thereof are in the centre of interest of, inter alia, medicine, molecular biology, and the industry producing plant protection products.

HSPs that are formed as a result of an external trigger as described above are generally referred to as 'inducible HSPs'. In addition, so-called 'constitutive HSPs' exist, which are formed on a more continuous basis, so as to serve in daily maintaining the function and architecture of (the cells of) the tissue. Constitutive HSPs e.g. accompany the synthesis and folding of proteins, and prevent the synthesis and accumulation of misformed cellular constituents.

U.S. Pat. No. 6,737,086 describes a biologically active alcoholic extract from a plant which exhibits Crassulacean acid metabolism (CAM), for example of *Opuntia fiscus-indica*. This composition is claimed to act on the cells of tissues or of living organisms by stimulating the autogeneous HSP production, when the cells are subjected to stress involving the synthesis of HSPs. The extract of *Opuntia fiscus-indica* may e.g. be used to amplify the synthesis of HSP90 in fibroplasts of human skin.

There is a tangible need for a large variety of skin care products for various cosmetic or medical purposes. For instance, skin care may be directed to avoiding or repairing skin damage as a result of one or more of various factors. Common examples of such factors are exposure to heat (which may result in burns), cold, drought, radiation, such as UV radiation (for example solar radiation, which may result in sun-burn), ionizing radiation (for example as a result of cancer treatment or exposure to radioactive nuclear compounds), rough surfaces (which may result in abrasion of the skin), and exposure to substances that are harmful to the skin.

Skin care may also be directed to treat or delay the visible signs of aging of the skin, e.g. by slowing down aging of the skin and/or by rejuvenating the skin. Various aspects may be addressed herein, e.g. wrinkling of the skin, sagging of the skin, loss of elasticity, age spots, and hyperpigmentation.

Further, the type of skin (e.g. dry, oily, sensitive (to e.g. solar radiation or physical contact), dark, light), may be a considerable factor influencing the effectiveness of a specific skin care product to achieve a specific desired effect, which generates a demand for a diversity of skin care products.

Further, the need for hypo-allergenic or even anti-allergenic skin care products poses additional requirements to these products.

It is an objective of the invention to provide a novel skin-care product that may serve as an alternative to known skin care products. This objective is met by providing a skin care composition comprising a specific stress protein or hydrolysate thereof.

Accordingly, the present invention relates to a skin-care product comprising at least one component selected from the group of plant heat shock proteins and plant heat shock protein hydrolysates.

A product according to the invention may in particular have one or more of the following effects: (1) healing or recovery of the skin after damage has occurred due to e.g. burns, abrasions, cuts (e.g. cuts generated during shaving), pimples, allergic reactions, poisoning, exposure to radiation (e.g. UV radiation, such as solar radiation, or ionizing radiation, such as radioactive radiation from e.g. radiation therapy or exposure to radioactive nuclear compounds), chemotherapy, contact of the skin with a substance (e.g. chemicals, clothing, soap, make-up, organic matter such as plant fluids or plants), mechanical friction (e.g. shoes, clothing, harnesses, horses), dehydration, bedsores, the application of a tattoo, piercing the skin (e.g. for decorative purposes); (2) recovery and/or maintenance of the homeostasis in the skin during and/or after homeostatic imbalance occurred due to a disease, due to the treatment of a disease, or due to exposure to e.g. heat, cold, drought, radiation, allergenes, poison, substances that are harmful to the skin; (3) curing of a skin disease or skin disorder, e.g. acne, warts, althlete's foot, Lyme disease, psoriasis, lichen, ichthyosis, keratosis, Darier's disease, pustulosis, herpes zoster, cellulitis, eczema (such as atopic dermatitis), neurodermatitis, herpes, inflammatory skin disorders, children's diseases affecting the skin (such as varicella, rubella, measles); (4) reduction of one or more visible signs of aging of the skin or rejuvenation of the skin, e.g. one or more effects selected from the group of reducing the number and/or the depth of wrinkles, smoothening the skin (including reducing cellulite), restoring the elasticity, reducing the intensity, size and number of age spots and reducing hyperpigmentation.

In the context of the present invention, with homeostasis, in particular homeostatic balance in the skin, is meant the maintaining of the internal environment at a constant level or between certain limits. Examples of the variables that may be controlled in homeostasis are pH, temperature, water potential, redox state, and the concentration of e.g. oxygen, carbon dioxide, glucose, certain vitamines, certain hormones, certain proteins, and certain salts.

A product according to the invention may in particular be suitable for persons who want to reduce one or more of the visible signs of aging of the skin or who want to rejuvenate the skin. It is herein understood that aging of the skin may occur by intrinsic aging and/or by extrinsic aging. Intrinsic aging is also known as the natural aging process, which comprises e.g. a reduced production of elastin in the skin, a reduced production of collagen in the skin, a slower removal of dead skin cells, a slower generation of new skin cells. Visible signs of intrinsic aging are e.g. wrinkles, thin and/or transparent skin, loss of underlying fat, sagging skin, dry skin, itching skin. Extrinsic aging usually occurs by one or more external factors that prematurely age the skin, e.g. one or more factors selected from the group of exposure to radiation of the sun, exposure to heat, exposure to cold, exposure to substances that are harmful to the skin, repetitive facial expressions, gravity, sleeping positions and smoking.

A product according to the invention may in particular be suitable for people or animals who have an impaired production of endogenous HSP, or who are not capable of producing endogenous HSPs at all. It may for example be suitable for elderly people (more than 50, more than 60 or more than 70 years of age) or for people having scar tissue in or on their skin.

The production of an endogenous HSP in skin of a subject is in particular considered impaired, if the start of the endogenous HSP production after exposure of skin cells of the subject to a trigger for inducing endogenous HSP is delayed (i.e. an increased response time) and/or if the endogenous HSP production (per hour) is reduced, after exposure to the trigger. A particularly suitable trigger is exposure of the skin cells to a temperature of 43° C. (as described in U.S. Pat. No. 6,737,086).

The skin cells (keratinocytes and/or fibroblasts) can be taken from the subject and incubated in a manner known in the art per se. HSP levels can be determined as described in S. Sanchez et al., Radiation Research 167 (2007) 572-580.

By comparing produced amount of endogenous HSP and/or response time with a normal reference value (from cells with normal HSP production, preferably from a subject of about the same age, the same sex and the same or a similar skin type), it can be established whether endogenous HSP production is impaired. The produced amount can suitably be determined after 1 hour, after 2 hours, after three hours or after a longer exposure, depending on the minimum response time that is considered normal for a specific subject. For example, in U.S. Pat. No. 6,737,086 it was reported that in human skin cells originating from a five-year-old subject HSP90 production occurred after 1 hour of exposure to a temperature of 43° C.

In impaired skin cells, the response time may in particular be increased by a factor of at least 1.5, at least 3, or at least 6. In impaired skin cells, the total amount of produced endogenous HSP (after 1 hr, after 2 hrs or after 3 hrs) may in particular be reduced by a factor of at least 1.5, at least 3, or at least 6.

A product according to the invention may also be suitable for persons who have or may develop a weathered skin due to repeated exposure of the skin to one or more members selected from the group of heat, cold, drought, chemicals, organic matter, allergens and (solar) radiation, such as construction workers (including specialists such as electricians, carpenters, pipefitters, welders and plumbers), workers in the exploration of oil and gas, roadworkers, chemical/pharmaceutical researchers, gardeners, kitchen workers (e.g. chefs, cooks, cleaners), factory workers.

A product according to the invention may also be effective to prevent developing striae in the skin or to reduce striae in the skin. With striae is meant scarring of the skin as a result of 1) rapid stretching (stretch marks') of the skin associated with rapid growth or weight gain that overcomes the dermis's elasticity and 2) hormonal changes in a body. Accordingly, a product according to the invention may for example be suitable for children (1-12 yr), adolescents (12-18 yr), body builders, pregnant women, women who have given birth.

It is envisaged that a product according to the invention may in particular be effective to recover an homeostatic balance (including rehydration) of skin that is being or has been exposed to solar radiation. It is also envisaged that it may be effective in repairing DNA and/or in removing cellular constituents of cells that have died during or after exposure of the skin to solar radiation.

Accordingly, a product according to the invention may in particular be a sunscreen product or an after sun product. In the context of the present invention, a sunscreen product is a product (e.g. a lotion, cream, spray, gel) that absorbs or reflects the sun's ultraviolet radiation and protects the skin. In the context of the present invention, an after sun product is a product that is applied to the skin after exposure of the skin to solar radiation, with the aim to aid the skin in its recuperation.

A product according to the invention may be a make-up product, as it is envisaged that the presence of make-up on a skin may be an appropriate way of contacting the skin with HSPs or hydrolysates thereof. It may also be advantageous to include HSPs or hydrolysates thereof in make-up removers, because skin often needs recovery after make-up has been removed.

A product according to the invention may in particular be an after shave product, as it is envisaged that shaving the skin may have one or more collateral effects such as cuts, abrasions, irritated skin, degraded skin due to contact with soap or homeostatic imbalance of the skin. Inclusion of HSPs or hydrolysates thereof in an after shave may therefore aid cosmetic skin-care or skin repair, or at least in a faster recovery of homeostatic balance in the skin. Accordingly, a product according to the invention may in particular be suitable for people who have to shave frequently and/or for people who have a sensitive skin in that shaving their skin more often leads to one or more of the above collateral effects.

A product according to the invention may be used to treat a skin disease or skin disorder selected from the group of acne (for example adolescents), warts, athlete's foot, Lyme disease, psoriasis, lichen, ichthyosis, keratosis, Darier's disease, pustulosis, herpes zoster, cellulitis, eczema (such as atopic dermatitis), neurodermatitis (such as lichen simplex chronicus, prurigo nodularis, lichen striatus or atopic dermatitis), herpes, inflammatory skin disorders and children's diseases affecting the skin (such as varicella, rubella, measles). In particular, people or animals who suffer from such a skin disease or skin disorder may be treated.

A product according to the invention may be suitable for use by people or animals to whose skin a tattoo has been applied and/or whose skin has been pierced. With a tattoo is meant a permanent marking, for example an image, made by inserting ink into the skin with the aid of a sharp object such as a needle. Tattoos on humans usually serve as decorative body modification, while tattoos on animals usually aim at improved identification or branding. With piercing of the skin is meant the practice of puncturing or cutting a part of the body, creating an opening in which an object may be worn, for example jewelry. The skin of animals may be pierced to allow them to wear for example an identification tag.

It is envisaged that a skin product according to the invention may positively affect the recuperation of skin that has undergone tattooing and/or piercing, for example by reducing or preventing formation of scar tissue and/or inflammation of the skin and/or underlying tissue.

A product according to the invention may also be effective to combat oxidative stress in the skin, and/or the damage that may result from such stress. With oxidative stress is meant a disturbance in the normal redox state of a cell, caused by an imbalance between the production of reactive oxygen compounds for metabolic purposes and the cell's ability to readily eliminate reactive intermediates and/or by-products that are formed from such reactive oxygen compounds. Such reactive intermediates and/or by-products may cause damage to components of the cell, such as one or more components selected from the group of proteins, lipids, and DNA.

As pointed out above, the formation of inducible HSPs in an organism may be induced by exposure of the organism to (extreme) changes in the environment, such as heat, (solar) radiation, chemicals, organic matter. It is an advantage of a product according to the invention that an increased of HSP level in an organism can be reached in the absence of such (extreme) changes in the environment, because the HSPs in a product according to the invention are themselves non-cytotoxic and do not cause substantial stress in the organism.

Compared to a (clinical) product comprising mammalian or microbial HSP, it is further considered that the HSP in a product according to the invention is advantageous in that specific contaminations are generally absent, that may be present in mammalian HSP or microbial HSP, e.g. pathogenic viruses or prions in the case of mammalian HSP or endotoxins in case of microbial HSP.

Besides the advantageous effects as outlined, it is envisaged that the HSP or HSP-hydrolysate from alfalfa or another plant is advantageous in that it is hypo-allergenic or anti-allergenic compared to e.g. microbial/mammalian HSP or microbial/mammalian HSP-hydrolysate.

HSP or HSP-hydrolysate from alfalfa is particularly preferred. HSP from alfalfa has a high similarity with HSP from humans, making it particularly suitable for use in the treatment of humans. For example, the peptide segments relevant for immune response in HSP70 from alfalfa shows, in contrast with HSP70 from other organisms, no differences in amino acid sequence between human HSP70, as can be seen in Table 1 and Table 2.

TABLE 1

| first segment: | | |
|---|---|---|
| Human[1] | LNVLRIINEPTAAAIAYGLD | #differences human SEQ |
| Alfalfa[2] | LNVLRIINEPTAAAIAYGLD | 0 |
| Mycobacterium | LNVLRIVNEPTAAALAYGLD | 2 |
| Maize | LNVMRIINEPTAAAIAYGLD | 1 |
| Tobacco | LNVMRIINEPTAAAIAYGLD | 1 |
| Tomato | LDVLRIINEPTAASLAYGFE | 5 |
| Wheat | LRVLRIINEPTAAAIAYGLD | 1 |

[1]amino acid positions 167-186
[2]amino acid positions 171-190

TABLE 2

| second segment | | |
|---|---|---|
| Human[3] | NPDEAVAYGAAVQAAIL | #differences human SEQ |
| Alfalfa[4] | NPDEAVAYGAAVQAAIL | 0 |
| Mycobacterium | NPDEVVAVGAALQAGVL | 5 |
| Maize | NPDEAVAYGAAVQAAIL | 0 |
| Tobacco | NPDEAVAYGAAVQAAIL | 0 |
| Tomato | NPDEVVALGASVQAGIL | 4 |
| Wheat | NPDEAVAYGASVQAAIL | 1 |

[3]amino acid positions 364-380
[4]amino acid positions 370-386

Furthermore, HSP or HSP-hydrolysate from alfalfa is preferred because of its relatively high ATPase activity. For example, alfalfa HSP70 has a higher ATPase activity than HSP70 from *Trypanosoma cruzi* (see Louw et al., Protein Expression and Purification 69 (2010), p 168-177) and is also expected to have a higher ATPase activity than human HSP70.

In a preferred embodiment, the HSP or HSP hydrolysate used in the present invention comprises a combination of HSP70 and HSP40 or a combination of hydrolysates thereof. HSP40 is expected to act as a co-chaperone and may thus improve the efficiency of HSP70, for example by increasing the ATPase activity of HSP70.

Further, it is envisaged that in at least some embodiments the HSP or HSP hydrolysate in a product of the invention may have an anti-allergenic effect and/or an anti-inflammatory effect.

A product according to the invention may be in particular be applied on mammalian skin, more in particular on human skin.

The term "or" as used herein is defined as "and/or" unless specified otherwise.

The term "a" or "an" as used herein is defined as "at least one" unless specified otherwise.

When referring to a moiety (e.g. a compound) in the singular, the plural is meant to be included, unless specified otherwise.

A product in accordance with the invention generally is a product comprising HSP or hydrolysate thereof that has been separated, in particular isolated from the source (the plant or part thereof) wherein it has been produced.

It is contemplated that at least in some embodiments HSP or HSP hydrolysate may be negatively affected by an alcohol, for instance ethanol. Accordingly, it is advantageous to use no alcohol or only as a minor component (e.g. in aqueous liquid) during the recovery process of the HSP from the source and during the preparation of the skin-care product.

A product according to the invention may in particular be selected from the group of creams, lotions, powders, gels, foams, oils, sprays (e.g. aerosol sprays), mousses, salves, balms, and pencils.

More in particular, a product according to the invention may be selected from the group of moisturizing compositions, anti-aging compositions, lip balms (e.g. against cracked lips), lipsticks, massage oils, body lotions, make-ups (e.g. make-up pencils), sunscreens, deodorants, aftershaves, perfumes, depilatory creams and skin peeling compositions.

A product according to the invention may in particular be sold in a cosmetic packaging, such as cosmetic flexible tubes, laminated tubes, bottles, jars, cans, revolving tubes (such as for releasing lipstick or lip balm). Material for such packaging may be selected from the group of glass, ceramic, metal, polypropylene, polyethylene and polyethyleneterephtalate. Further, the cosmetic packaging may comprise a component selected from the group of coatings, screw caps and spray pumps.

The HSP is usually obtained from a plant, e.g. from a fluid from a plant or from a plant extract. Suitable methods to obtain the HSP are known in the art per se, for instance from EP 1 531 160 A1.

Preferably, the HSP is a natural, i.e. non-recombinant, HSP; the HSP-hydrolysate preferably is a hydrolysate from natural (non-recombinant) HSP. It is contemplated that a natural HSP or hydrolysate of natural HSP may be tolerated better by the subject treated with the skin-care product, in particular that the risk of allergenic reactions may be less. Further, consumer acceptance may be better for non-recombinant plant HSP.

A product according to the invention may comprise native HSP or denaturated HSP.

A product according to the invention may in particular comprise heat shock proteins or heat shock protein hydrolysates from alfalfa (*Medicago sativa*).

Optionally, in addition or alternatively the skin care product comprises HSP or HSP-hydrolysate from another plant. Other plants as a source of HSP may in particular be selected from the group of cereals (for instance barley), soy, grasses (for instance oat), peas, beet, potato, clover and water plants (for instance an alga).

In particular, leaves of the plant may be used as source for one or more HSPs. Particularly suitable are beet tops, alfalfa leaves, barley leaves, oat leaves and potato tops.

With HSP-hydrolysate is meant HSP wherein part of the chemical bonds have been hydrolysed, in particular peptide bonds. Generally, for achieving an intended cosmetic or medical effect, non-hydrolysed HSP may be particularly suitable. It is however contemplated that in some embodiments, the presence of HSP-hydrolysate may be advantageous. For example, it is contemplated that hydrolysed HSP may penetrate better into (the cells of the skin.

The HSP-hydrolysate may be prepared by, e.g., chemical hydrolysis, enzymatic hydrolysis or a combination thereof. Chemical hydrolysis may for example be performed in an aqueous medium of neutral pH, or in an aqueous medium in the presence of an acid (e.g. a strong acid such as HCl) or a base (e.g. a strong base such as NaOH). The hydrolysis (chemical and/or enzymatic) may be carried out at an elevated temperature. The enzymatic hydrolysis may in particular be performed with a proteolytic enzyme, based on technology known per se. Enzymatic hydrolysis is an effective alternative to chemical hydrolysis, because it is relatively mild in comparison to acid or alkali hydrolysis. Additionally, the inherent specificity of a specific proteolytic enzyme of choice can control the nature and extent of hydrolysis, and thus the functional properties of the end product.

The degree of hydrolysis may be chosen within wide limits. At least 10 wt. %, at least 25 wt. %, at least 50 wt. %, at least 80 wt. % or at least 90 wt. % (based on the sum of HSP-fragments and unhydrolysed HSP) of the HSP-hydrolysate may be formed by HSP fragments. Of the HSP-hydrolysate, 100 wt. % or less, 95 wt. % or less, at least 75 wt. % or less, 50 wt. % or less or 25 wt. % or less (based on the sum of HSP-fragments and unhydrolysed HSP) may be formed by HSP fragments.

The size of the fragments may be chosen within wide limits. Usually, in case a hydrolysate is present, at least 50 wt. %, in particular at least 75 wt. %, more in particular at least 90 wt. % (based on the sum of HSP-fragments and unhydrolysed HSP) of the hydrolysate is formed by peptides (including unhydrolysed HSP) having at least five amino acid residues. In a specific embodiment, at least 25 wt. %, in particular at least 50 wt. %, more in particular at least 75 wt. % (based on the sum of HSP-fragments and unhydrolysed HSP) of the hydrolysate is formed by peptides (including unhydrolysed HSP) having at least ten amino acid residues.

The skin-care product may in particular comprise at least one HSP or hydrolysate thereof selected from the group of HSP40, HSP60, HSP70 and HSP90, respectively hydrolysates of any of these HSPs. In particular, HSP70 or a hydrolysate thereof is preferred.

The concentration of HSP, HSP hydrolysate, or a mixture thereof in a product according to the invention may be chosen within wide limits, usually in the range of 10 to 10 000 μg per 100 mL of product; preferred compositions depend on the type of product and its intended use.

The concentration of HSP, HSP hydrolysate, or a mixture thereof may be at least 100 μg per 100 mL, in particular at least 400 μg per 100 mL of skin-care product. The concentration of HSP, HSP hydrolysate, or a mixture thereof may be 1000 μg or less per 100 mL, in particular 600 μg or less per 100 mL of skin-care product.

For a clinical skin care product, the total concentration of HSPs, HSP hydrolysates, or a mixture thereof may advantageously be in the range of 500-5000 μg per 100 ml of product.

In a specific embodiment, the skin care product is a clinical product for treating parts of the skin that are severy damaged (e.g. third degree burns or damage after intense skin contact with a corrosive chemical), wherein the total concentration of HSPs, HSP hydrolysates, or a mixture thereof may be chosen in the range of 1000-5000 μg per 100 mL of product.

The skin care product may further comprise known ingredients for a specific skin care product, e.g. for a sunscreen, for a lip balm, for a moisturizing cream, for a body lotion, for a massage oil, for a make-up, for a deodorant, for an aftershave, for a perfume, for a make-up pencil, for a scrub crème, for a peeling crème, for a depilatory cream. Suitable examples of known ingredients are for example UV blocking agents, preservatives, stabilizers, moisturizers, antioxidants, vitamins, fragrances, thickening agents, chalk, ceramides, emulsifiers, surfactants, minerals, alkaloids, enzymes, co-enzymes, acids, polyphenols, ceramides, herbs, plant extracts, solvents, amino acids, oil lipids, pH adjuster, salts, polysaccharides, fatty acids, flavonoids, hormones, yeast extracts, matrix metalloproteinases, peptides, emoillents.

A skin care product may be based on commercially available or otherwise known formulations to which HSP or HSP-hydrolysate is added, e.g. on a known salve, (lip) balm, lotion, mousse, cream, oil, powder, gel, foam, spray, deodorant, perfume, after shave or pencil. Examples of known skin care compositions are for example given in WO 01/85129 A2.

Usually, the ingredients of the skin care product, including the HSP or HSP hydrolysate, are dissolved or emulsified in a lipophilic medium, which may comprise one or more components selected from the group of triglycerides, such as capric triglyceride, C18-C36 alkyl acid triglycerides; acrylates, such as C10-C30 alkyl acrylates; oils, such as olive oil, sunflower oil, sclerocarya birrea oil, lime oil, nut oil, manuka oil, mineral oil, rapeseed oil, teatree oil; hydroxyethyl urea; isodecyl laurate; fatty acids such as stearic acid; and phospholipids such as lecithine.

In particular, in a spray, the ingredients may be suspended or emulsified in a propellant, which may comprise one or more components selected from the group of chlorofluorocarbons such as 1,1,1,2-tetrafluoroethane, trichlorotrifluoroethane; hydrocarbon gases such as propane, isobutane and isopentane; dimethyl ether; carbon dioxide; and nitrogen gas.

In addition to the HSP or HSP-hydrolysate, a product according to the invention may comprise one or more other active agents, e.g. a co-chaperone for the HSP or HSP-hydrolysate. However, the product may also be free of such additional agents. It is contemplated that the HSP or HSP-hydrolysate may be capable of interacting with an endogenous (formed in situ by the subject) co-chaperone or the like.

In addition, one or more preserving agents may be present such as sorbate, benzoate, sulfite, or the like.

As will be understood by the skilled person, the composition is formulated to be safe for administration to the skin.

The HSP or HSP hydrolysate in a product according to the invention may be incorporated in a carrier, preferably a cosmetically or pharmaceutically acceptable carrier. It may for example be incorporated in a liposome or a microcapsule.

In the context of the invention liposomes are defined as composite structures comprising lipids, in particular phospholipids, and may contain small amounts of other molecules. The sizes of liposomes are usually in the range of 20 nm to 1000 nm. They may for example be at least 40 nm, at least 100 nm or at least 250 nm. The liposomes may for example be 800 nm or less, 600 nm or less or 400 nm or less.

It is envisaged that a carrier, in particular a liposome that comprises an HSP or a hydrolysate thereof may be capable of effective delivery of an HSP respectively a hydrolysate thereof into cells of the skin.

It is further envisaged that incorporation of an HSP and/or a hydrolysate thereof in a carrier may result in an increased stability of the HSP respectively the hydrolysate thereof, for example because of a decreased exposure of the HSP respectively the hydrolysate thereof to (atmospheric) oxygen. Accordingly, the shelf life of a product according to the invention may also be increased by incorporation of HSP and/or a hydrolysate thereof in a carrier.

The invention further relates to the use of at least one compound selected from the group of plant heat shock proteins and plant heat shock protein hydrolysates for cosmetic care. The use of HSP or hydrolysate thereof for cosmetic care may in particular comprise the use of HSP from alfalfa, respectively HSP hydrolysate from alfalfa.

The cosmetic care may in particular be directed to slowing down the aging of the skin and/or rejuvenating the skin. The cosmetic care may more in particular be directed to reaching one or more cosmetic effects selected from the group of reducing the number and/or the depth of wrinkles, smoothening the skin (including reducing cellulite), restoring the elasticity, reducing the intensity, size and number of age spots and reducing hyperpigmentation.

The invention further relates to a compound selected from the group of heat shock proteins and heat shock protein hydrolysates, in particular plant heat shock proteins and plant heat shock protein hydrolysates, preferably as identified above, for therapeutical treatment of the skin. The compound may be a heat shock protein or heat shock protein hydrolysate selected from the group of HSP40, HSP60, HSP70 and HSP90, respectively hydrolysates thereof. In particular, HSP70 or a hydrolysate thereof are preferred. Preferably, the compound according to the invention is derived from alfalfa.

A compound according to the invention may in particular be used for avoiding or treating skin damage. It may for example be used for avoiding or treating skin damage due to an occurrence selected from the group of burns, abrasions, cuts (e.g. cuts occurring during shaving), pimples, allergic reactions, poisoning, exposure to radiation (e.g. solar radiation or radioactive radiation such as radiation from radiation therapy), chemotherapy, contact of the skin with a skin-damaging substance (e.g. corrosive chemicals, irritant organic matter such as particular plant fluids or particular plants), mechanical friction (e.g. shoes, clothing, harnesses, horses), dehydration, bedsores, the application of a tattoo and piercing the skin (e.g. for decorative purposes).

A compound according to the invention may further be used for the treatment of a skin disease or skin disorder selected from the group of acne, warts, althlete's foot, Lyme disease, psoriasis, lichen, ichthyosis, keratosis, Darier's disease, pustulosis, herpes zoster, cellulitis, eczema (such as atopic dermatitis), neurodermatitis, herpes, inflammatory skin disorders and children's diseases affecting the skin (such as varicella, rubella, measles).

The invention further relates to a method for the therapeutic treatment of a subject suffering from at least one complaint selected from the group of skin damage, skin disease and skin disorder, comprising administering to the skin a composition comprising at least one component selected from the group of plant heat shock proteins and plant heat shock protein hydrolysates, preferably as identified above.

The skin damage may in particular comprise healing the skin after damage has occurred due to an occurrence selected from the group of burns, abrasions, cuts, pimples, allergic reactions, poisoning, exposure to radiation, chemotherapy, contact of the skin with a skin-damaging substance, mechanical friction, dehydration, bedsores, the application of a tattoo and piercing the skin.

The skin disease or skin disorder may in particular be a disease or disorder as mentioned above.

The subject usually is a mammal, in particular a human, which may be an infant (<1 yr), an older child (1-12 yr), an adolescent (12-18 yr), or an adult in his early (19-39 yr), middle (40-65 yr) or late adulthood (>65 yr).

The treatment in general comprises the administration on the skin by e.g. spraying onto the skin, applying onto the skin by an applicator, such as a roller, a brush or a sponge, or by manual application.

The dosage of HSP or hydrolysate thereof may be chosen within wide limits, depending on the intended use, the subject and the way of administration. As a rule of thumb a suitable average daily dosage is chosen in the range of 0.01 µg and 1 mg per square meter of skin. Usually, the average daily dosage is 0.1 µg per square meter of skin or more, in particular 0.5 µg per square meter of skin or more. Usually, the average daily dosage is 100 µg per square meter of skin or less, in particular 10 µg per square meter of skin or less.

The skin care product may be administered e.g. once a week; preferably the skin care product is administered at least once a day. The product may be administered a plurality of times per day, e.g. 2-10 times, 2-6 times or 2-3 times. The product may be present in or on a plaster that is applied on at least a part of the skin that is in need of treatment. Advantageously, such plaster gradually releases the amount of skin care product that is intended to administered, for example in 24 hours or less, in 12 hours or less, in 6 hours or less or in 3 hours or less.

The invention is further directed to a method for preparing a skin care product, comprising the mixing of a carrier material with at least one component selected from the group of heat shock proteins from alfalfa or another plant and heat shock protein hydrolysates from alfalfa or another plant.

The invention further relates to a method for preparing a skin care product according to the invention, comprising
    providing plant HSP, in particular HSP from alfalfa, isolated from the plant the HSP originates from, optionally hydrolysing the HSP or part thereof, and
    combining the HSP or HSP hydrolysate, with one or more skin care product ingredients, in particular one or more ingredients for a specific skin care product, as mentioned herein.

The plant HSP may be provided in a manner known per se. For instance, the plant HSP may be a plant HSP obtained by a method described in EP-A 1531160, of which the contents—in particular the claims and examples—are incorporated herein by reference.

In particular the HSP may be a plant HSP obtained by a method according European patent application with application number 09157774.2 (filed on 9 Apr. 2009, applicant Alfa Biogene International B.V.), of which the contents—in particular the examples, suitable process conditions and suitable materials for use in the method—are incorporated herein by reference.

More in particular the plant HSP may be obtained by a method for recovering HSP
    obtaining a liquid comprising the HSP from the plant;
    precipitating one or more components other than the HSP from the liquid;

adding a fibrous filter aid and a mineral powder to the liquid; then subjecting the liquid comprising the HSP, precipitated component(s), the fibrous filter aid and the mineral powder to a first filtration step over a filter, thereby separating the precipitate, fibrous filter aid and mineral powder from the filtrate comprising the stress protein; thereafter subjecting the filtrate to a further filtration step; and thereafter purifying the HSP. The purified HSP may then be used in a method for preparing a skin care product according to the present invention.

In said method for recovering the HSP, the mineral powder preferably comprises at least one granular mineral, in particular at least one granular mineral selected from the group of diatomaceous earth and perlite.

In said method for recovering the HSP, the fibrous filter aid preferably comprises cellulose fibres.

In said method for recovering the HSP the fibrous filter aid preferably is a mixture of fibres having a different length, the mixture at least providing fibres with a length over the range of about 20☐m to about 130☐m.

In said method for recovering the HSP the further filtration step to which the filtrate is subjected may in particular be an depth filtration step.

In said method for recovering the HSP, after the further filtration step, a fraction comprising stress protein may be subjected to a fluid removal step thereby concentrating the stress protein in the fraction, preferably by reversed osmosis, ultrafiltration or nanofiltration, and/or to a salt removal step, preferably by dialysis.

The purification of HSP may in particular comprise chromatography. The chromatography preferably comprises a first strong anion exchange step, thereafter an affinity chromatography separation step, and thereafter a second strong anion exchange step. Suitable strong ion exchange separation materials are in particular those comprising trialkylammoniumalkyl functional groups, preferably trimethyl ammoniumethyl (TMAE) functional groups. The affinity chromatography materials may in particular be selected from chromatography materials for nucleotide-based affinity separation, preferably an adenosine based affinity separation, more preferably an ATP or ADP based affinity separation, even more preferably an affinity separation on ATP-agarose, ATP-sepharose, ATP-polyacrylamide, ATP-silica or ATP cellulose The median particle size of the exchange material used in the first anion exchange is preferably larger than the median particle size of the exchange material used in the second anion exchange.

If desired the HSP or part thereof may be hydrolysed, e.g. as described herein above.

The plant HSP or hydrolysate may be combined with the additional skin care product ingredients in a process for preparing the skin care product in a manner that is otherwise known per se, e.g. it may be combined with one or more other proteins and/or peptides (if present) which combination can then be further processed to produce the skin care product of interest. Depending on the skin care product, it is also possible to add the HSP or hydrolysate to the skin care product already comprising the other ingredient(s).

The invention will be illustrated by the following examples.

EXAMPLE 1

Sequence Alignment

A sequence alignment was conducted to compare HSP70 protein sequences of different species with the human HSP70 protein sequence. The results of the sequence aligment is shown in Table 3.

The sequence alignment was conducted with the LALIGN software (see http://www.ch.embnet.org/software/LALIGN form.html). The following parameters were used:
alignment method: local (default)
number of reported sub-alignments: 3
opening gap penalty: −14
extending gap penalty: −4

TABLE 1

| Sequence Identity | |
| --- | --- |
| Sequence Alignment | Sequence Identity (%) |
| Human/Alfalfa | 76 |
| Human/Barley | 66.1 |
| Human/Maize | 75.2 |
| Human/Rice | 75.2 |
| Human/Soy | 74.3 |
| Human/Tomato | 48.5 |

EXAMPLE 2

Effect of Alfalfa HSP70 Containing Skin Cream on Wound Healing of Radiation Burns Two groups of at least 20 mice each are provided. The mice in both groups undergo dermal radiation injury via an ortho-voltage irradiator on a defined area of the skin.

After injury, all animals are bandaged. Furthermore, to the radiation wounds of the mice in the first group (test group) a first skin cream is applied, which cream contain 20 μg alfalfa HSP70 per ml. A second skin cream is applied to the radiation wounds of the mice in the second group (control group), which cream is similar to the first cream, but does not contain any HSP70.

Assessment of wound healing is carried out by assessing a part (at least 5 mice) of the control and the test group at different days, viz. at the start of the treatment (baseline) and 1 day, 3 days, 5 days and 10 days after injury. The assessment comprises colour photographs of the wound and collection and analysis of margin and wound tissues by microscopy and/or immunocytology.

EXAMPLE 3

Effect of Alfalfa HSP70 Containing Skin Cream on Psoriasis and/or Neurodermatitis A group of at least 20 patients suffering from psoriasis and/or neurodermatitis is treated with an alfalfa HSP70 containing skin cream and a placebo. Each patient is treated by applying an alfalfa HSP70 containing skin cream on the affected skin areas of one side of the body and a placebo to the affected skin on the contralateral side of the body for at least 6 weeks twice per day (in the morning and in the evening). The skin cream contains 20 µm alfalfa HSP70 per ml skin cream.

Assessment of the affected skin of the patients is carried out at different times during the treatment, viz. at the start of the treatment, after 3 days, after 1 week, after 3 weeks and after 6 weeks. Colour photographs of the patients' faces are taken and microtopography parameters of the skin surface are recorded by utrasound measurements.

The invention claimed is:

1. A skin-care product comprising at least one component selected from the group consisting of heat shock proteins from alfalfa and heat shock protein hydrolysates from alfalfa, wherein the heat shock protein or heat shock protein hydrolysate is selected from the group consisting of HSP40, HSP60, HSP70 and HSP90, and respectively hydrolysates thereof.

2. A skin-care product according to claim 1, wherein the skin-care product is a product selected from the group consisting of creams, lotions, powders, gels, foams, oils, sprays, mousses, salves, balms, and pencils.

3. A skin-care product according to claim 1, wherein the skin-care product is a product selected from the group consisting of moisturizing compositions, anti-aging compositions, lip balms, lipsticks, massage oils, body lotions, make-ups, sunscreens, deodorants, aftershaves, perfumes, depilatory creams and skin peeling compositions.

4. A skin-care product according to claim 1, wherein the heat shock proteins or heat shock protein hydrolysates are present in a concentration of 100-1000 µg per 100 mL.

5. A skin-care product according to claim 1, comprising liposomes comprising a compound selected from the group consisting of heat shock proteins or heat shock protein hydrolysates.

6. A method of cosmetically treating skin comprising contacting the skin with at least one compound selected from the group consisting of heat shock proteins from alfalfa and heat shock protein hydrolysates from alfalfa, wherein the heat shock protein or heat shock protein hydrolysate is selected from the group consisting of HSP40, HSP60, HSP70 and HSP90, and respectively hydrolysates thereof.

7. The method according to claim 6, wherein the compound is contacted to the skin to slow down the aging of the skin and/or rejuvenate the skin.

8. The method according to claim 6, wherein the compound is contacted to the skin resulting in one or more cosmetic effects selected from the group consisting of reducing the number and/or the depth of wrinkles, smoothening the skin, restoring the elasticity, reducing the intensity of age spots, reducing the size of age spots, reducing the number of age spots, and reducing hyperpigmentation.

9. A method of medically treating skin comprising contacting the skin with a compound selected from the group consisting of heat shock proteins from alfalfa and heat shock protein hydrolysates from alfalfa, wherein the heat shock protein or heat shock protein hydrolysate is selected from the group consisting of HSP40 HSP60 HSP70 and HSP90 and respectively hydrolysates thereof.

10. The method according to claim 9 wherein the compound is contacted to the skin resulting in treatment of skin damage due to an occurrence selected from the group consisting of burns, sunburns, abrasions, cuts, pimples, allergic reactions, poisoning, exposure to radiation, chemotherapy, contact of the skin with a substance, mechanical friction, dehydration, bedsores, the application of a tattoo and piercing the skin.

11. The method according to claim 9 wherein the compound is contacted to the skin resulting in the treatment of a skin disease or a skin disorder selected from the group consisting of acne, warts, althlete's foot, Lyme disease, psoriasis, lichen, ichthyosis, keratosis, Darier's disease, pustulosis, herpes zoster, cellulitis, eczema, atopic dermatitis, neurodermatitis, herpes, inflammatory skin disorders, children's diseases affecting the skin, varicella, rubella, and measles.

12. The method according to claim 9 wherein the compound is contacted to the skin resulting in the treatment of psoriasis or neurodermatitis.

13. A method for prophylactic or therapeutic treatment of a subject suffering from skin damage, skin disease or skin disorder, comprising administering to the skin a composition comprising at least one component selected from the group consisting of heat shock proteins from alfalfa and heat shock protein hydrolysates from alfalfa, wherein the heat shock protein or heat shock protein hydrolysate is selected from the group consisting of HSP40, HSP60, HSP70 and HSP90, and respectively hydrolysates thereof.

14. The method according to claim 13, wherein the prophylactic or therapeutic treatment comprises treating the skin that has been damaged due to an occurrence selected from the group of burns, abrasions, cuts, pimples, allergic reactions, poisoning, exposure to radiation, chemotherapy, contact of the skin with a skin-damaging substance, mechanical friction, dehydration, bedsores, the application of a tattoo and piercing the skin.

15. The method according to claim 13, wherein the disease or disorder is selected from the group consisting of acne, warts, althlete's foot, Lyme disease, psoriasis, lichen, ichthyosis, keratosis, Darier's disease, pustulosis, herpes zoster, cellulitis, eczema, atopic dermatitis, neurodermatitis, herpes, inflammatory skin disorders, children's diseases affecting the skin, varicella, rubella, and measles.

16. A method for preparing a skin-care product comprising the steps of providing isolated plant HSP from alfalfa, optionally hydrolysing the isolated plant HSP or part thereof, and combining the HSP or HSP hydrolysate, with one or more skin-care product ingredients, wherein the heat shock protein or heat shock protein hydrolysate is selected from the group consisting of HSP40, HSP60, HSP70 and HSP90, and respectively hydrolysates thereof.

17. The skin-care product according to claim 1, wherein the heat shock proteins or heat shock protein hydrolysates are present in a concentration of 400-600 µg per 100 mL of skin-care product.

18. The skin-care product of claim 1 wherein the heat shock protein from alfalfa is HSP70.

19. The method of claim 6 wherein the heat shock protein from alfalfa is HSP70.

20. The method of claim 9 wherein the heat shock protein from alfalfa is HSP70.

21. The method of claim 13 wherein the heat shock protein from alfalfa is HSP70.

22. The method of claim 16 wherein the heat shock protein from alfalfa is HSP70.

23. The method of claim 6 wherein the skin has been damaged and the skin is treated by the at least one compound selected from the group consisting of heat shock proteins from alfalfa and heat shock protein hydrolysates from alfalfa in a manner to heal or recover the skin.

24. The method of claim 9 wherein the skin has been damaged and the skin is treated by the at least one compound selected from the group consisting of heat shock proteins from alfalfa and heat shock protein hydrolysates from alfalfa in a manner to heal or recover the skin.

25. A skin-care product comprising at least one component selected from the group consisting of heat shock proteins from alfalfa and heat shock protein hydrolysates from alfalfa wherein at least 50 wt. % of the hydrosylate is formed by peptides having at least five amino acid residues.

26. A skin-care product comprising at least one component selected from the group consisting of heat shock proteins from alfalfa and heat shock protein hydrolysates from alfalfa wherein at least 25 wt. % of the hydrosylate is formed by peptides having at least ten amino acid residues.

27. A method of cosmetically treating skin comprising contacting the skin with at least one compound selected from the group consisting of heat shock proteins from alfalfa and heat shock protein hydrolysates from alfalfa wherein at least 50 wt. % of the hydrosylate is formed by peptides having at least five amino acid residues.

28. A method of cosmetically treating skin comprising contacting the skin with at least one compound selected from the group consisting of heat shock proteins from alfalfa and heat shock protein hydrolysates from alfalfa wherein at least 25 wt. % of the hydrosylate is formed by peptides having at least ten amino acid residues.

29. A method of medically treating skin comprising contacting the skin with a compound selected from the group consisting of heat shock proteins from alfalfa and heat shock protein hydrolysates from alfalfa wherein at least 50 wt. % of the hydrosylate is formed by peptides having at least five amino acid residues.

30. A method of medically treating skin comprising contacting the skin with a compound selected from the group consisting of heat shock proteins from alfalfa and heat shock protein hydrolysates from alfalfa wherein at least 25 wt. % of the hydrosylate is formed by peptides having at least ten amino acid residues.

31. A method for prophylactic or therapeutic treatment of a subject suffering from skin damage, skin disease or skin disorder, comprising administering to the skin a composition comprising at least one component selected from the group consisting of heat shock proteins from alfalfa and heat shock protein hydrolysates from alfalfa wherein at least 50 wt. % of the hydrosylate is formed by peptides having at least five amino acid residues.

32. A method for prophylactic or therapeutic treatment of a subject suffering from skin damage, skin disease or skin disorder, comprising administering to the skin a composition comprising at least one component selected from the group consisting of heat shock proteins from alfalfa and heat shock protein hydrolysates from alfalfa wherein at least 25 wt. % of the hydrosylate is formed by peptides having at least ten amino acid residues.

33. A method for preparing a skin-care product comprising the steps of providing isolated plant HSP from alfalfa, optionally hydrolysing the isolated plant HSP or part thereof, and combining the HSP or HSP hydrolysate, with one or more skin-care product ingredients, wherein at least 50 wt. % of the hydrosylate is formed by peptides having at least ten amino acid residues.

34. A method for preparing a skin-care product comprising the steps of providing isolated plant HSP from alfalfa, optionally hydrolysing the isolated plant HSP or part thereof, and combining the HSP or HSP hydrolysate, with one or more skin-care product ingredients, wherein at least 25 wt. % of the hydrosylate is formed by peptides having at least five amino acid residues.

* * * * *